United States Patent [19]

Leiser

[11] 4,310,628
[45] Jan. 12, 1982

[54] FRUCTOSE PRODUCTION
[75] Inventor: Roger S. Leiser, Decatur, Ill.
[73] Assignee: A. E. Staley Manufacturing Company, Decatur, Ill.
[21] Appl. No.: 130,276
[22] Filed: Mar. 14, 1980

Related U.S. Application Data

[63] Continuation of Ser. No. 662,199, Feb. 26, 1976, abandoned.

[51] Int. Cl.$^3$ .......................... C12P 19/24; C12N 9/92
[52] U.S. Cl. ...................................... 435/94; 435/234; 435/813
[58] Field of Search ................. 435/94, 188, 234, 813, 435/174, 177, 179, 180, 181

[56] References Cited

U.S. PATENT DOCUMENTS

| | | | |
|---|---|---|---|
| 3,847,741 | 11/1974 | Heady et al. | 435/94 |
| 3,979,261 | 9/1976 | Outtrup | 435/94 |
| 4,025,389 | 5/1977 | Poulsen et al. | 435/94 |

OTHER PUBLICATIONS

Yoshimura et al., "Studies on D-Glucose Isomerizing Activity of D-Xylose Grown Cells from *Bacillus coagulans*, Strain HN-68" *Agr. Biol. Chem.,* vol. 30, No. 10, (1966), pp. 1015-1023.
Danno, "Studies on D-Glucose-Isomerizing Enzyme from *Bacillus Coagulans,* Strain HN-68", *Agr. Biol. Chem.,* vol. 34, No. 12 (1970), pp. 1805-1814.
Dixon et al., *Enzymes,* Academic Press Inc., New York, (1964), pp. 116-119 and 144-151.
Zittan et al., "Sweetzyme—A New Immobilized Glucose Isomerase", *Die Starke,* vol. 27, No. 7, (1975), pp. 236-241.

*Primary Examiner*—Thomas Wiseman
*Attorney, Agent, or Firm*—M. Paul Hendrickson; Charles J. Meyerson

[57] ABSTRACT

Fructose productivity and isomerase activity in immobilized beds or column operations employing isomerases obtained from Bacillus organisms are significantly improved by isomerizing a high solids feed syrup at pH 7.0-7.5 and 55° C. to 60° C. Without adding cobalt to the feed streams, continuous column operation in excess of 4,000 hours and yielding greater than 3,500 pounds of a 42% fructose syrup for each pound of isomerase can be achieved.

11 Claims, No Drawings

FRUCTOSE PRODUCTION

This application is a continuation of U.S. patent application Ser. No. 662,199, entitled "Fructose Production" filed Feb. 26, 1976, now abandoned, by Roger S. Leiser.

BACKGROUND OF THE INVENTION

Fructose obtained by enzymatically isomerizing dextrose to fructose is extensively used by the food industry as a sucrose replacement.

Substantial fructose production costs are encountered by the need to frequently replace spent or deactivated glucose isomerases. Enhanced fructose productivity by glucose isomerase is a desirable goal. Extensive research efforts have been expended towards obtaining maximum fructose productivity with the lowest possible amount of glucose isomerase. Many researchers have deemed the solution to the problem as being simply a matter of discovering a stable glucose isomerase. In this endeavor, the art has screened, mutated and prepared a multitude of different glucose isomerase preparations. In testing the efficacy and susceptibility of these glucose isomerases to deactivation, the art has come to the realization that isomerases derived from different microbe sources possess different enzymatic characteristics. Optimum isomerization conditions such as pH and temperature, isomerase activators (e.g., metal ion activators such as $Co^{++}$, manganese, etc.) and other processing variables will depend upon particular glucose isomerase type. In general, a greater disparity in isomerization conditions occurs between isomerases derived from a different genera.

Immobilized isomerases are more stable than isomerases in a water-soluble or unbound form. In general, immobilized glucose isomerases are better suited for commercial operations since they may be continuously used in batch or continuous operations until exhausted. Upon exhaustion, these isomerases are replaced with fresh immobilized isomerase. Most isomerization reactions are conducted at temperatures and pHs which optimize the rate at which the isomerase converts dextrose to fructose. Similar to other enzymes, isomerases are usually most stable against inactivation (including heat inactivation) and possess a higher enzymatic activity when used at their optimum isomerization pH. Glucose isomerases presently used in the commercial production of fructose containing syrups characteristically exhibit improved stability and activity when the isomerization process is conducted in the presence of $Co^{++}$ ions. Cobaltous salts are occasionally added to feed syrups for this purpose. It would be desirable to achieve a higher productivity without necessitating cobaltous ions.

A suggested glucose isomerization processing modification is to increase the isomerization reaction temperature as isomerase activity decreases. An increase in the reaction temperature will accelerate the rate of fructose production as well as the rate at which the isomerase deactivates. The net effect is to lower the total fructose yield produced by the isomerase.

Isomerases reportedly produced by organisms belonging to the Bacillus genera include *Bacillus stearothermophilus* ATCC 31265, NRRL B-3680, NRRL B-3681 and NRRL B-3682; *Bacillus* sp. NRRL B-5350 and NRRL B-5351; *Bacillus megaterium* ATCC 15450; *Bacillus fructosus* ATCC 15451, 35c. (e.g., see U.S. Pat. Nos. 3,826,714 by Suekane et al. and 3,306,752 by K. Ueda, West German printed patent application No. 2,164,342 filed under Ser. No. P 2,164.342.5 on Dec. 23, 1971 by K. Aunstrup et al., Agri. Biol. Chem., Vol. 31, No. 3, pages 284–292, 1967 by Danno et al.). Heat or chemical treatment of viable cells containing intracellular isomerase, encapsulation, complexing with natural and synthetic polymers, immobilization within a binder matrix and numerous other means for immobilizing isomerases have been suggested. Exemplary methods for immobilizing isomerases and enhancing enzymatic stability are disclosed in J. Appl. Chem. Biotechnol. 1974, 24, 663–676 by Kent et al. Agri. Biol. Chem., Vol. 30, No. 10, pages 1015–1023, 1966 by S. Yoshimura et al. (e.g., see Holland patent application No. 73/12525 filed Sept. 11, 1973 and assigned to Novo Terapeutisk Laboratorium, British Patent Specification No. 1,274,158, U.S. Pat. Nos. 3,821,082 by Lamm et al., 3,779,869 by Zienty 3,694,314 by Lloyd et al., 3,788,945 by Thompson et al., and British Patent Specification No. 1,356,283 by Monsanto Co., etc.).

A recent article entitled "Sweetzyme—A New Immobilized Glucose Isomerase," die Starke 27, Jahrg 1975/Nr. 7, pages 236–241 discloses immobilized isomerases of a *Bacillus coagulans* origin. This article defines glucose isomerase productivity as the combined effect of activity and stability. At the more neutral pHs, cobalt is deemed essential for fructose productivity. In order to achieve optimum fructose syrup productivity in the absence of cobalt ions, the authors conclude that it is necessary to conduct the continuous isomerization reaction at a relatively high alkaline pH. For a continuous operation (e.g., column isomerization) involving a short contact and reaction time between isomerase and syrup, optimum productivity (in the absence of $Co^{++}$) is reportedly achieved at a pH above 8.0 (e.g., 8.1–8.5), a 40–45% solids level and 65° C.

OBJECTS

It is an object to prolong the useful life and fructose productivity of immobilized glucose isomerases of a Bacillus origin.

Another object is to improve the processing efficacy of isomerizing glucose to fructose in column type reactors.

A still further object is to continuously isomerize a dextrose syrup to a fructose syrup under processing conditions which alleviates the formation of undesirable by-products.

THE INVENTION

According to the present invention, there is provided a process for improving fructose syrup productivity by isomerizing dextrose to fructose within an immobilized glucose isomerase bed in which the isomerase is characterized as being obtained from the Bacillus genera and exhibiting an enhanced rate of isomerizing dextrose to fructose when the glucose isomerization reaction is conducted: (a) in the presence of $Co^{++}$ ions and (b) at a temperature greater than about 60° C., said process comprising:

(A) providing a refined dextrose syrup which is essentially free from $Co^{++}$ ions and containing on a total dry solids weight basis at least 90% monosaccharide, (B) isomerizing the dextrose syrup to a fructose syrup by passing the dextrose syrup through a bed of immobilized glucose isomerase maintained at a temperature of no more than about 60° C. and a pH between 7.0 and 7.5, (C) recovering the fructose syrup while replenishing the bed with fresh dextrose syrup, and (D) continuing the isomerization of the dextrose syrup in said bed until the total isomerase bed activity has been reduced to a value of less than 20% of its original activity thus achieving improved fructose syrup production from said bed.

The present process employs a refined dextrose syrup having a high monosaccharide solids content and essentially free from $Co^{++}$ ions. The present invention may be used in a process in which a reactor produces the desired fructose syrup product in a single pass or by recycling the syrup through a reactor at a higher flow rate until the desired interconversion is achieved or with a plurality of reactors connected in series wherein the fructose content is incrementally increased as the syrup flows through each reactor in the series.

Productivity of the isomerization process is generally enhanced by employing feed syrups of a high monosaccharide content. High dextrose conversion syrups containing more than 90% dextrose (dry solids weight basis—d.s.b.) or 95% dextrose or higher (especially at about 97 to 99%) are particularly useful feed syrups (e.g., see U.S. Pat. Nos. 3,783,100 by R. Larson et al. and 3,897,305 by T. Hurst).

The isomerized syrup quality and glucose isomerase bed productivity are adversely affected by inorganic and organic, non-saccharide syrup contaminants. Certain metal ions, in trace quantities, such as aluminum, copper, tin, zinc, mercury, calcium, etc. and anions which inactivate the isomerase and/or react to form insolubles, can reduce bed productivity. Such contaminants may be removed from the dextrose feed syrup by conventional cation and anion resin treatment. Incomplete ion exchange treatment can also lead to the development of insoluble floc or precipitates in the isomerization system causing pressure drops in the isomerization column reactor which reduces bed productivity. These ionic impurities may be suitably removed from the high dextrose feed syrup by single or double cation and anion exchange treatment (e.g., strong cation-weak anion-strong cation-weak anion).

Organic substances typically present in high dextrose conversion syrups such as proteinaceous materials, color (e.g., HMF) and flavor contaminants, etc. have a deleterious effect upon bed productivity and fructose syrup quality. Conventional ion exchange treatment cannot remove all of these undesirable organic substances from the feed syrup. Such organic substances may be conveniently removed from the syrup by conventional means such as granular carbon, activated carbon treatment (e.g., at levels of about 0.5 to about 2.0 parts by weight activated carbon for each 100 parts by weight dry syrup solids). Insoluble organic and inorganic substances are also desirably removed by conventional means from the feed syrup prior to the isomerization reaction. Refining the syrup by the sequential steps of removing the insolubles, carbon treatment and ion exchange treatment is generally satisfactory.

The present isomerization reaction is conducted at temperatures, pH levels and other operating conditions which are conducive to microbial growth. Without adequate safeguards against microbial growth, the isomerization reactors upon prolonged usage can become infested. This will adversely affect isomerase productivity and syrup quality. By adjusting the feed syrup dry solids to more than 45% by weight, and preferably at least 50% by weight, the microbial infestation problem is more easily controlled. Feed syrups containing more than 60% dry solids are generally too viscous for effective passage through the isomerization reactor. A feed syrup adjusted to a dry solids level ranging from about 50% to about 55% by weight will generally provide adequate flow rates through the reactor while minimizing microbial infestation. Periodic or continuous treatment of the feed syrups with conventional bactericides can be used as a processing aid to reduce microbial infestation.

In the present process, dextrose is isomerized to fructose by passing a dextrose syrup through an immobilized bed containing an isomerase derived from an organism of the Bacillus genera. Suitable immobilized beds for conducting the isomerization reaction include conventional techniques and apparatus for confining the immobilized isomerase within an isomerization reaction zone while permitting the passage of syrup through the bed. Column type reactor systems operated in a single pass or recycling or a plurality of reactors connected in series may be utilized to convert the syrup to the desired fructose containing syrup product (e.g., fructose to dextrose weight ratio between about 2:3 to about 1:1). Preferably, the isomerization process is conducted by continuously permitting a dextrose syrup to flow through a column reactor containing immobilized glucose isomerase with the amount of glucose isomerase and flow rate of syrup through the column being sufficient to increase the fructose syrup content to a level between about 44 to about 47% (monosaccharide weight basis).

The isomerases employed in this invention are characterized as exhibiting an optimum isomerase activity within the range of 8.0–8.5 as determined under standard assay conditions with an assay substrate of 60 grams water, 40 grams anhydrous dextrose, 0.02 M magnesium sulfate, 0.0035 M cobalt chloride at 65° C. for one hour. Under these assay conditions, the isomerase will produce more fructose between pH 8.0–8.5 than will be produced outside this range. If the above standard assay temperature is reduced (e.g., 60° C. or less), these isomerases (under these assay conditions) produce less fructose than they will at 65° C. or higher. Another characteristic of the isomerase is that when cobalt chloride is excluded from the standard assay substrate and the assay is conducted at pH 7.5 and 60° C. for one hour, the fructose production will be less than that produced when 0.0035 M cobalt chloride is included as an assay ingredient.

Although the isomerization process generally applies to immobilized isomerases which are derived from the Bacillus genera, the invention is particularly adapted for use with isomerases obtained from the *Bacillus coagulans* family (e.g. NRRL B-5305 and NRRL B-5351) and immobilized in accordance with Netherlands patent application No. 73/12525 filed on Sept. 11, 1973. These isomerases are more stable against inactivation when used in an isomerization process with a stabilizing amount of $Co^{++}$ ion (e.g., between 0.0015–0.004 M), possess a pH optimum of about 8.5 and optimum isomerization temperature well above 60° C.

In practicing the invention, column type reactors may be suitably loaded with isomerase typically having an activity (per the standard assay conditions mentioned above) greater than about 400 IGIU/gram of enzyme. The bed advantageously contains greater than about $3 \times 10^6$ IGIU and preferably more than about $6 \times 10^6$ IGIU/per cubic foot of bed volume. When it is desired to produce about 45% fructose (monosaccharide basis) in a single pass, column loading so as to permit an initial syrup flow rate through a fresh bed of about 0.05 to about 0.2 gallon/min. (usually at about 0.1) for each cubic foot of bed volume is generally suitable. The flow rate is proportionally reduced to compensate for deactivation of the bed as the isomerization process proceeds.

The enzymatic isomerization is conducted at a pH between 7.0 to less than about 7.5. If the pH drops below the 7.0 level, the isomerase (without the presence of a stabilizing amount of $Co^{++}$) is susceptible to permanent deactivation. At a pH in excess of 7.5, the total fructose productivity of the bed will similarly decrease because of isomerase deactivation. An ancillary advantage of operating the isomerization process within this more neutral pH range is that it prevents formation of undesirable flavor and color bodies. In comparison to a pH 8.5 and 65° C. process, fructose productivity of the bed is enhanced under the present process from about 5 to 10 fold. This enhanced fructose productivity substantially reduces the overall total isomerase requirements to produce a given amount of fructose, and enables one to operate the reactor for a longer period of time without interrupting its operation to reload. Similar to other enzymes, isomerases are typically more sensitive to deactivation when used at a pH substantially below their optimum pH. Contrary to expectations, the total bed fructose productivity is significantly increased by conducting the isomerization reaction without a stabilizing amount of cobalt (e.g., more than 0.001 M) at a pH level which is well outside its optimum isomerization pH range.

During the isomerization process, the dextrose rich syrup migrates into the immobilized isomerase particles. Within the particles, the dextrose is isomerized to a fructose rich syrup. This fructose rich syrup migrates from the particle and the particles are replenished with fresh dextrose. Thus, similar to exchange of fluids in living organisms, heterogenity between the external syrup phase and the internal particle phase exists. Certain dry immobilized isomerase preparations, such as those prepared in accordance with Netherlands Patent Specification No. 73/12525, have been found to contain latent acidic substances (e.g., glutaraldehyde crosslinked type of immobilized isomerases). These acidic substances are apparently initially held tightly within the structure of the dry immobilized particle. When used in an isomerization process, these acids are entrapped within the particles. The entrapped acids can create an excessively low localized pH and cause inactivation of the isomerase.

Adequate processing precautions should be taken to prevent these acids from deactivating the isomerase. This problem can be conveniently alleviated by hydrating and neutralizing the acid-containing dried immobilized particles with a non-deactivating base (e.g., sodium hydroxide, bicarbonate and carbonate of sodium, etc.), prior to commencement of the isomerization reaction (e.g., immediately after loading), or by adding an isomerase compatible, water-soluble base or buffer to the feed syrup in an amount sufficient to ensure maintenance of the pH between about 7.0–7.5.

The isomerization pH may be maintained within the pH 7.0–7.5 range by adding to the feed syrup or reactor a non-deactivating base (e.g., sodium hydroxide, bicarbonate, carbonate, etc.) or conventional buffers which will not deactivate the isomerase (e.g., sodium sulfite, sodium bisulfites, carbonates, etc.). Non-degradative reducing agents conventionally added by the corn syrup manufacturer to prevent oxidation and formation of color bodies may be incorporated into the feed syrup such as sodium bisulfite.

Although the process is conducted in the absence of heat stabilizing amounts of cobalt ions, the isomerization reaction is conducted in the presence of co-metal ion isomerase activator. The co-metal activity requirements will often vary between different isomerases (e.g., those obtained from different microbial sources). Valence two metal ions such as magnesium are known and often used in isomerization as metal co-activators. These metal ion co-activators are normally incorporated into the isomerization media as a salt (e.g., sulfate, bisulfite, citrate, acetate of magnesium, etc.). When a *Bacillus coagulans* derived isomerase is used in the process, the presence of magnesium ions and its concentration will affect overall fructose productivity. Although the magnesium ion molarity can range between about 0.001 M to about 0.01 M for a Bacillus derived isomerase improved productivity is obtained when the isomerization media contains at least about 0.002 M magnesium ion. Above the 0.01 M level, the magnesium ion requirements of the isomerase are met and any further amounts thereof merely reflect in increased processing costs (e.g., magnesium salt costs and additional burden upon refining systems to remove the ions, etc.). A magnesium ion content between about 0.003 M to about 0.010 M has been found to be particularly effective for enhancing total isomerase productivity.

The bed is used until the bed activity decreases to less than 20% and preferably less than 15% of its maximum operational activity rating. Typically, fresh immobilized isomerase will have an assay activity (per the standard assay condition mentioned above) of at least 400 International Glucose Isomerase Units (i.e., IGIU) per gram and will typically be used in the continuous process until it has an activity rating of less than 80 IGIU/gm. The most appropriate syrup flow rates through the column or bed will depend upon the desired degree of fructose conversion, bed isomerase activity, bed flow and pressure drop characteristics. In order to maintain a constant fructose yield (e.g., about 45% fructose and 55% dextrose), the feed syrup flow rate is proportionally regulated so as to coincide with the isomerase activity of the bed. For example, a bed loaded with 30 pounds of isomerase per cubic foot of an isomerase activity of 500 units/gram (i.e., 6,810,000 $IGIU/ft.^3$) and a desired output of about 45% fructose, will typically be initially operated at a flow rate of about 0.1 gallon per minute (gpm)/cubic foot of bed ($ft.^3$). However, when the isomerase activity decreases to about 50 IGIU/gram (i.e., 681,000 $IGIU/ft.^3$) a slower syrup flow rate of 0.01 $gpm/ft.^3$ is needed to provide an equivalent fructose yield. Typical terminal syrup flow rates are greater than 0.005 $gpm/ft.^3$ and most usually above about 0.01 $gpm/ft.^3$. It is, however, desirable to use the highest possible flow rates. Total bed activity, however, limits the rate at which the syrup may be passed through the column to achieve the desired fructose level. Below the 40 IGIU/gm. level, the flow rates are so slow that the process becomes uneconomical. For most column operations, the syrup flow rate will range between about 0.01 to about 0.2 $gpm/ft.^3$.

The immobilized isomerases under the isomerization conditions of this invention typically have an initial low activity (e.g., less than 200 IGIU/gm.) and produce a relatively low amount of fructose during the initial 10–15 hours of operation. In contrast, a bed operated at pH 8.5 characteristically has substantially higher activity and yields more fructose. A typically, however, the immobilized isomerase under the present processing conditions evinces a substantial activity increase after about 200–400 hours of use (e.g., 235 IGIU/gram or higher) while one operated at a higher pH and temperature will progressively decrease in activity. After about 400 hours, the immobilized isomerase gradually decreases in activity until the bed becomes spent (typically greater than 3,500 hours and preferably after at least 4,000 hours of continued use) as opposed to the rapid decrease experienced with immobilized beds operated at pH's above or below this level. The overall net effect of the processing conditions employed in this invention is to maintain a much higher level of fructose productivity over a more prolonged period of time.

The degree of permanent isomerase deactivation arising out of column operations conducted outside the prescribed pH 7.0–7.5 range is directly related to the extent the pH deviates therefrom and its exposure time. On an equivalent time basis, column operation at a pH above 8.5 or below 6.0 causes more extensive permanent deactivation and reduced productivity than operations conducted within pH 7.8–8.0 or 6.5–7.0 ranges. Operation at either a pH of about 6.0 to 8.5 for a short period of time (e.g., 24 hours), generally results in a lesser degree of inactivation than prolonged operation (e.g., 300 hours) at pH's of about 6.5 or 8.0.

Due to occluded or tightly bound acidic substances contained within the immobilized isomerase (e.g., glutaraldehyde, cross-linked immobilized isomerase), it is difficult to immediately achieve the desired pH 7.0–7.5 effluent level. Hydrating and neutralizing the isomerase bed (prior to commencing the isomerization process as mentioned above) accelerates the rate at which the bed will stabilize to a pH 7.0–7.5 (e.g., typically within a day). In contrast, the untreated beds will usually require at least two times more time for the effluent stream to stablize to a pH 7.0–7.5. Alternatively, buffers may be used as a processing aid to maintain the pH within the prescribed pH 7.0–7.5 range. In the event neither buffers nor a pretreated isomerase are used and the isomerase bed contains a relatively high level of occluded acid, the pH of the influent stream may be temporarily adjusted to a slightly higher pH (e.g., 7.5–8.0 and at higher flow rates) in order to compensate for the acidic bed substances and achieve the desired pH 7.0–7.5 effluent stream.

It is important during the initial 2,000 hours of column operation to maintain the isomerase bed, as reflected by effluent stream pH, at a pH of at least 7.0 up to a pH 7.5. Enchanced isomerase productivity will be accomplished by operating the column within this range at least 90% of the operational time, and most preferably more than 95% of the operation time at pH 7.0–7.5. As a general rule, the isomerase bed under the process conditions herein typically retain more than 40% (often 50% or more) of its original 24 hour activity rating after 2,000 hours of continued use. During the latter life cycle of the isomerase bed (e.g., after 3,000 hours), maintaining the pH within 7.0–7.5 will enhance productivity to a lesser degree. Its effect upon productivity is less because of the substantially reduced level of bed potency or activity. In the preferred embodiments of the invention, the pH is maintained within the 7.0–7.5 range for at least 90% of its operational life with no more than 5% of the total operational time being above pH 8.0 or below 6.5. Substantial and permanent isomerase inactivation occurs when the process is conducted for 100 hours or more above pH 8.0 or below pH 6.5. If the pH deviates from the pH 7.0–7.5 range, isomerase activity is partially restorable by readjusting the pH to the 7.0–7.5 level. This, however, doesn't correct the permanent isomerase degradation and productivity loss which has been caused by operating outside the 7.0–7.5 pH range.

Temperature has a similar effect upon fructose productivity. Elevated temperatures temporarily increase bed activity, but decrease its overall productivity. The equation: $\ln_e Y = 14.484 - (0.10247)(X)$, wherein Y is fructose productivity and X is the isomerization temperature (in C°.), closely approximates the affect of temperature upon productivity in the present process. Short intermittent exposure to elevated temperature may occur, but is desirably avoided. Comparative to a 65° C. process, a 60° C. or lower operational temperature initially produces less fructose. Equivalent fructose production (i.e., total fructose yield) at the 60° C. isomerization temperature is typically not accomplished until after 1400 hours of continuous operation, at which time, the 60° C. fructose productivity approaches or begins to exceed the 65° C. productivity. The isomerase bed remains operationally viable at 60° C. for a longer time period than at the 65° C. level (e.g., 4,050 hours vs. 1,680 hours). Improved productivity is accomplished by maintaining the column reactor below 61° C. for at least 90% of its operational life, and preferably at about 60° C., or less, for at least 95% of its operational period. If desired, the column reactor temperature may be increased to 65° C. or higher, when the bed approaches the state of exhaustion. Operational temperatures below 55° C. do not adversely affect the productivity of the isomerase bed but the reaction rate is substantially slower. When the operational temperature decreases below the 55° C. level, the high solids syrups used herein become more viscous and less mobile. Microbial infestation of the bed is also difficult to prevent at the reduced operational temperatures. From an overall processing viewpoint, it is advantageous to conduct the isomerization reaction between the 57° C. to 61° C. range.

In the continuous production of high fructose conversion syrups, conventional batch assay tests and conventional techniques employed to ascertain optimum operational conditions are misleading and frequently inapplicable to the overall conditions needed to achieve maximum productivity. These conventional assay tests (e.g., IGIU assay tests) are useful in determining the initial isomerase potency or activity rating and its suitability for use in a continuous high fructose syrup operation. Thereafter the most meaningful guideline is the total amount of fructose actually produced by a given amount of enzyme. In a continuous high fructose syrup process, the amount of fructose produced by the isomerase bed at any time during its operation (as well as the total amount of fructose which has been produced) may easily be determined by monitoring the effluent stream. Periodic monitoring of the effluent stream enables one to ascertain when the isomerase has reached its maximum level of production. Thereafter, the bed efficency, during any stage of the process, can be determined by comparing the monitored level of fructose production with its maximum level of fructose production. In the present process, the bed is advantageously used until the amount of fructose produced by the bed decreases to a value of less than 15% of its maximum fructose output (i.e., its highest monitored fructose production or activity level). Preferably the reactor bed is replenished or replaced with fresh isomerase when the bed activity decreases to within about 10% to about 15% of its maximum output level.

In general, the isomerization conditions of this invention can extend the useful and productive life of an immobilized isomerase by at least 2,000 hours. By maintaining the pH within the pH 7.0–7.5 and below 61° C., the present process typically permits the fructose syrup manufacturer to continuously operate the column reactor and achieve adequate fructose interconversion for more than 3,000 hours and most typically more than 4,000 hours. The anticipated useful bed life in a pH 8.5 and 65° C. process is less than 1,000 hours. The present process produces a higher quality fructose syrup. Syrup degradation arising from the isomerization process is nominal with minimum off-flavor and off-color development. The present syrups can be placed in a useable form without necessitating extensive carbon and ion exchange treatment.

The following examples are merely illustrative and should not be construed as limiting the scope of the invention.

EXAMPLE I

This example illustrates improved dextrose productivity employing an immobilized glucose isomerase identified as "Novo SP-113E" sold by Novo Enzyme Corporation, 1830 Mamoroneck Avenue, Mamoroneck, N.J. 10543, in a single pass column type reactor under the isomerization conditions of this invention. The enzyme was derived from Bacillus coagulans immobilized by glutaraldehyde crosslinking under Netherlands Patent Application No. 73/12524.

The dry immobilized isomerase was hydrated and neutralized at pH 7.5 and 50° C. for one hour, by slurrying 20 grams dry isomerase in 150 ml. refined 95–96% dextrose syrup (at 50% dry solids) which contained 0.005 M $MgSO_4 \cdot 7H_2O$ adjusted to pH 7.5 (sodium hydroxide). The sodium hydroxide treated and highly swollen isomerase slurry was then transferred to a water-jacketed, column reactor (height 30 cm and 2.5 cm diameter).

In this example, a 50% dry weight solids, 97.5% D.E., 96% dextrose, 2.5% disaccharide, 0.5% trisaccharide and 1.5% polysaccharide (D.P. 4 or higher) feed syrup was used. The syrup was refined by treating it at pH 4.0–4.5 with 0.5–1.0% powdered, activated carbon, removing the insolubles therefrom by filtration, followed by ion exchanging with a strong cation resin (Rohm & Haas Amberlite 252), weak base anion (Diamond Shamrock Duolite ES-561), strong cation (Amberlite 252), and then a weak base union (Duolite ES-561) connected in series. The refined syrup was adjusted to pH 7.5 (sodium hydroxide) with 0.005 M $MgSO_4 \cdot 7H_2O$ (as a metal ion activator), and 0.8 grams methyl paraben, 0.2 grams propyl paraben and 1.97 grams sodium benzoate (as preservatives) being added thereto (grams/syrup liter basis). The refined dextrose feed syrup (at 60° C.) was continuously fed to the column reactor at a flow rate ranging between 0.6–2.4 ml. feed syrup/minute.

The pH of the influent or dextrose feed syrup stream was maintained at about 7.5 and the effluent pH stream was periodically monitored. During the initial stages of the isomerization reaction (at about 24 hours), the effluent stream pH gradually increased from 6.0 to the desired 7.0–7.5 range. Thereafter the effluent stream pH essentially remained within the 7.0–7.5 range excepting monitored pH's of 6.9 at 336 hours and 689 hours and 8.0 at 2177 hours and 8.5 at 2201 hours. Illustrative monitored flow rates, percent of total dextrose isomerized to fructose, bed isomerase activity, total cumulative fructose yields or productivity and effluent pH values (approximately 24±7 hours basis) are tabulated in Table 1.

For comparative purposes a column reactor was then operated under essentially the same conditions including the 60° C. feed syrup, except a pH 8.5 dextrose feed syrup was used. The results of this comparative test are reported in Table 2.

TABLE 1

| TIME, HRS | FLOW CC/MIN | MEAS. RI | MEAS. RϕTA | PERCENT FRUCTOSE | ACTIVITY U/G ENZ. | PRODUCTIVITY | EFF. pH | FEED PH |
|---|---|---|---|---|---|---|---|---|
| 17 | 1.53 | 1.4132 | 8.6 | 34.1 | 1589 | 26.8 | 6.1 | 7.5 |
| 24 | 2.08 | 1.4135 | 14.6 | 31.0 | 1819 | 38.6 | 6.9 | 7.5 |
| 43 | 2.03 | 1.4137 | 12.4 | 32.2 | 1897 | 73.6 | 7.2 | 7.5 |
| 67 | 1.50 | 1.4147 | 9.8 | 33.6 | 1532 | 114.5 | 7.2 | 7.5 |
| 93 | 1.93 | 1.4074 | 6.4 | 35.1 | 1995 | 160.0 | 7.3 | 7.5 |
| 113 | 1.88 | 1.4073 | 4.8 | 36.0 | 2043 | 200.0 | 7.2 | 7.5 |
| 168 | 1.94 | 1.4139 | 9.4 | 33.8 | 1985 | 313.3 | 7.2 | 7.5 |
| 236 | 1.83 | 1.4124 | −.4 | 38.9 | 2491 | 456.7 | 7.4 | 7.5 |
| 281 | 1.36 | 1.4130 | −7.0 | 42.4 | 2355 | 559.9 | 7.2 | 7.5 |
| 305 | 1.14 | 1.4112 | −7.4 | 42.7 | 1981 | 611.5 | 7.2 | 7.5 |
| 336 | 1.02 | 1.4118 | −7.6 | 42.8 | 1794 | 669.5 | 6.9 | 7.5 |
| 353 | 1.81 | 1.4130 | 4.8 | 36.2 | 2102 | 702.4 | 7.3 | 7.5 |
| 377 | 1.71 | 1.4132 | 4.6 | 36.3 | 2003 | 751.3 | 7.3 | 7.5 |
| 477 | 1.98 | 1.4137 | 10.0 | 33.4 | 1985 | 948.9 | 7.2 | 7.5 |
| 521 | 1.52 | 1.4114 | 5.0 | 36.0 | 1723 | 1031.2 | 7.4 | 7.5 |
| 545 | .67 | 1.4115 | −12.8 | 45.6 | 1506 | 1069.7 | 7.5 | 7.5 |
| 641 | 1.15 | 1.4151 | 4.2 | 36.5 | 1392 | 1209.0 | 7.0 | 7.5 |
| 737 | 1.90 | 1.4148 | 15.8 | 30.5 | 1634 | 1351.1 | 7.3 | 7.5 |
| 857 | 1.67 | 1.4134 | 14.0 | 31.3 | 1484 | 1516.2 | 7.5 | 7.5 |
| 953 | 1.52 | 1.4133 | 13.0 | 31.8 | 1389 | 1652.7 | 7.5 | 7.5 |
| 977 | 1.46 | 1.4139 | 12.6 | 32.1 | 1360 | 1685.5 | 7.5 | 7.5 |
| 1073 | 1.36 | 1.4114 | 10.8 | 32.9 | 1293 | 1808.8 | 7.5 | 7.5 |
| 1223 | 2.25 | 1.4143 | 29.2 | 23.4 | 1288 | 1990.8 | 7.4 | 7.5 |
| 1530 | 2.09 | 1.4153 | 34.4 | 20.8 | 1032 | 2333.4 | 7.5 | 7.5 |
| 1625 | 2.06 | 1.4139 | 32.6 | 21.5 | 1049 | 2432.2 | 7.4 | 7.5 |
| 2033 | 1.62 | 1.4138 | 28.6 | 23.6 | 936 | 2799.1 | 7.4 | 7.5 |
| 2153 | 1.35 | 1.4133 | 28.6 | 23.6 | 773 | 2898.0 | 7.4 | 7.5 |
| 2177 | .97 | 1.4143 | 23.4 | 26.4 | 663 | 2915.1 | 8.0 | 7.5 |
| 2201 | 2.61 | 1.4139 | 50.2 | 12.3 | 663 | 2930.9 | 8.5 | 7.5 |

TABLE 1-continued

| TIME, HRS | FLOW CC/MIN | MEAS. RI | MEAS. RφTA | PERCENT FRUCTOSE | ACTIVITY U/G ENZ. | PRODUC- TIVITY | EFF. pH | FEED PH |
|---|---|---|---|---|---|---|---|---|
| 2223 | 3.61 | 1.4140 | 39.0 | 18.2 | 1475 | 2954.2 | 7.5 | 7.5 |
| 2297 | 1.68 | 1.4147 | 38.6 | 18.6 | 708 | 3034.4 | 7.3 | 7.5 |
| 2489 | 1.37 | 1.4128 | 35.8 | 19.7 | 611 | 3162.1 | 7.3 | 7.5 |
| 2705 | 1.21 | 1.4116 | 34.6 | 20.1 | 548 | 3284.9 | 7.4 | 7.5 |
| 2900 | 1.06 | 1.4110 | 30.4 | 22.2 | 547 | 3386.7 | 7.4 | 7.5 |
| 3020 | 1.41 | 1.4138 | 43.4 | 15.8 | 484 | 3445.6 | 7.3 | 7.5 |
| 3094 | 1.60 | 1.4111 | 46.4 | 13.6 | 445 | 3479.4 | 7.3 | 7.5 |
| 3212 | 1.43 | 1.4120 | 44.4 | 14.9 | 447 | 3530.3 | 7.5 | 7.5 |

TABLE 2

| TIME, HRS | FLOW CC/MIN | MEAS. RI | MEAS. RφTA | PERCENT FRUCTOSE | ACTIVITY U/G ENZ. | PRODUC- TIVITY | EFF. pH | FEED PH |
|---|---|---|---|---|---|---|---|---|
| 17 | 1.22 | 1.4127 | −1.6 | 39.6 | 1733 | 29.2 | 7.6 | 8.5 |
| 24 | 2.31 | 1.4131 | 16.2 | 30.1 | 1916 | 41.9 | 8.4 | 8.5 |
| 43 | 2.21 | 1.4132 | 20.4 | 27.9 | 1622 | 75.3 | 8.4 | 8.5 |
| 93 | 1.85 | 1.4069 | 10.6 | 32.7 | 1664 | 147.3 | 8.4 | 8.5 |
| 113 | 1.84 | 1.4072 | 11.0 | 32.5 | 1641 | 180.1 | 8.4 | 8.5 |
| 168 | 1.82 | 1.4124 | 15.4 | 30.5 | 1530 | 266.6 | 8.4 | 8.5 |
| 281 | 2.15 | 1.4144 | 22.2 | 27.1 | 1525 | 328.7 | 8.3 | 8.5 |
| 305 | 2.73 | 1.4105 | 37.6 | 18.2 | 1080 | 492.9 | 8.3 | 8.5 |
| 353 | 1.83 | 1.4123 | 31.6 | 21.8 | 932 | 509.8 | 8.4 | 8.5 |
| 377 | 1.87 | 1.4127 | 34.0 | 20.6 | 886 | 531.3 | 8.5 | 8.5 |
| 477 | 1.63 | 1.4124 | 34.4 | 20.3 | 757 | 597.4 | 8.4 | 8.5 |
| 521 | 1.65 | 1.4102 | 26.4 | 24.3 | 956 | 653.6 | 8.4 | 8.5 |
| 545 | 1.61 | 1.4105 | 26.2 | 24.4 | 944 | 676.2 | 8.5 | 8.5 |

As shown in Table 1, isomerase activity and fructose yields for the 7.0–7.5 isomerization reaction was initially low but gradually increased to the optimum (monitored) insomerase activity of 2491 units/gram after about 10 days operation. The isomerase activity for the comparative pH 8.5 reaction was initially significantly higher and reached an optimum monitored activity after about one day. Although initial productivity for the pH 7.0–7.5 process, was lower than the pH 8.5 process its productivity exceeded the pH 8.5 process after about 5 days operation. After about 22.7 days operation the cumulative fructose productivity for the pH 7.0–7.5 reaction was 1069.7 versus 676.2 for the pH 8.5 syrup (Table 2).

As illustrated by the Table 1 data, isomerase activity and fructose productivity decreased when the effluent stream dropped below the pH 7.0 level but increased upon its subsequent restoration to the pH 7.0–7.5 range (e.g., compare the 305, 336 and 353 hour data). The Table 1 data also shows that an effluent pH of 8.0–8.5 will significantly reduce both the isomerase activity and fructose yields with higher fructose production levels occurring upon restoration to the pH 7.0–7.5 range (e.g., see 2153–2223 hour data). These excessive pH levels are undesirable even though it occurred late in the continuous process and they adversely affected overall fructose productivity of the bed.

Remaining or residual isomerase activity (based upon 17 hour activity at 100%) for the column reactor operated continuously with a pH 7.5 feed syrup and 3,000 hours was in excess of 30% and greater than 28% after 3,200 hours of continuous operation. On the basis of the isomerase beds maximum monitored activity level (236 hours), the 25% activity level or 75% deactivation did not occur until about 2,500 hours. About 2,978 hours of operational use were required for the bed to decrease to the 20% activity level with the calculated 15%, 12.5% and 10% activity levels respectively occurring at about 3,555 hours, 3,920 hours and 4,368 hours. Comparatively, the pH 8.5 feed reactor will yield a calculated 20% activity level at about 990 hours and 15% activity at 1,175 hours, a 12.5% at 1,292 hours and a 10% activity level after about 1,436 hours of operation. Total calculated productivity at the 10% activity rating (based on its maximum column activity rating) for the pH 7.5 feed is 3,873 and 1,017 for the pH 8.5 process. Average isomerase half-life for the Table 1 run was 1,389.64 hours versus 445.33 hours for the pH 8.5 Table 2 run.

The fructose-rich effluent stream of the Table 1 run was clearer, contained less contaminants and requires less refining to place it in a commercially acceptable form than the Table 2 run effluent stream.

In Tables 1 and 2 (from left to right) the continuous operational time is reported in the column headed (time/hrs.), the flow rate is cubic centimeters per minutes under the heading FLOW CC/MIN., MEAS. R.I. represents the refractive index of the effluent syrup (at 45° C.), the MEAS. RφTA is the optical rotation of the effluent fructose syrup (@20 cm cell path and 25° C.), the ACTIVITY U/G ENZ. is the calculated activity rating of the isomerase on unit per gram of isomerase basis, the PRODUCTIVITY column reports the total cumulative amount of syrup dry substance produced by the column upon the basis of isomerization to a 42% fructose syrup (dry solids basis), EFF. pH is the effluent stream pH with the feed pH being reported in the extreme right column.

The reported percent fructose values for the effluent stream were determined from the MEAS. R.I. and MEAS. RφTA values by the following computations:

Weight % dry substance or
"%d.s."=(487.74)(Meas.R.I.)−639.72

Specific Rotation or
"S.R."=(100)(MEAS.RφTA/(2.4)(% d.s.)

% Fructose or %F=38.7−(0.63)(S.R.)

The Activity UG/Enz. represents the isomerase activity of the bed (in fructose activity units/gram isomerase) at the specified time intervals which were computed as follows:

Isomerase equilibrium constant or $E.C.$ =
$$\frac{(0.513)(\% \text{ monosaccharide dry substance in feed syrup})^1}{100}$$

Activity $UG/Enz.$ =
$$\frac{(\% \ d.s.)(60)(cc/min.)(10)(1.2)(E.C.)}{\text{gms. enzyme}} \times \ln_e\left[\frac{E.C.}{E.C. - \% F/100}\right]$$

[1] Total % fructose and dextrose (dry substance weight basis) in feed syrup which was 96%.

wherein $\ln_e$ is the natural logarithm, 60 (cc/min.) represents feed syrup flow rate in cubic centimeters per hour and gms enzyme is the total grams of isomerase in the column.

Prior to column loading the initial activity rating for the "Sweetzyme E" immobilized isomerase employed in this Example (per the standard assay methodology mentioned above) was 600 Glucose Isomerase Units/gram of isomerase.[2]

[2] —In micromoles/min. vs Activity UG/Enz. in mg./hour

In a larger column operation, maintenance of the pH within the 7.0–7.5 range is easier (e.g., internal pH sensory devices) than in a smaller column operation. Similarly in a large column operation a constant percent fructose syrup content can be more easily controlled by an effluent stream fructose analyzer so as to permit manual or mechanical regulation of the feed syrup flow rate to yield a constant fructose level in the effluent fructose stream.

The dry immobilized glucose isomerase employed herein may be pretreated for 30 minutes at ambient temperatures (e.g., 23° C.) and pH 7.5 with dextrose feed which contains cobalt ion (e.g., 0.001 M cobaltous nitrate) and 0.02 M magnesium sulfite, for purposes of hydrating and assuring the isomerase contains its full complement loading of cabaltous ion prior to commencement of the isomerization run.

This example illustrates high fructose productivity without adding any cobaltous ions to the feed syrup. Although not illustrated herein, cobaltous ions in amounts such as employed in conventional isomerization operations (e.g., 0.001 M Co++) adversely affect isomerase productivity. If desired, low cobaltous ion concentrations (e.g., less than 0.0005 M), and advantageously at concentrations less than 0.00025 M Co++ (most preferably less than 0.00005 M) may be continuously added to the feed syrup stream. Alternatively, somewhat higher cobaltous ion concentrations (e.g., less than about 0.001 M) may be intermittently added to the feed syrup.

EXAMPLE II

Employing the refined dextrose syrup and column reactor system of Example I, two different feed syrups were continuously fed to separate glucose isomerization column reactors. The isomerase (Novo SP-113b) was derived from *Bacillus coagulans*, immobilized via glutaraldehyde cross-linking aand spray-dried per the disclosure of Netherlands Patent Application No. 73/12524. Screen analysis for the spray-dried immobilized isomerase was 69% on #20 sieve. In one run, a dextrose feed syrup containing 0.008 M sodium bisulfite (as a buffer) and 0.009 M epsom salt (MgSO$_4$·7H$_2$O—metal ion activator) at a pH 7.5 and 60° C. was continuously introduced to the column reactor at flow rates ranging between 1.62 to 6.18 cc/minute. The feed syrup in the comparative run was the same, excepting the feed syrup was adjusted to pH 8.5 without added sodium bisulfite buffer and maintained at a flow rate ranging from 0.80 to 4.54 cc/minute.

Similar to Example I, the pH 7.5 run was significantly more productive than the pH 8.5 run. After 1,891 hours continuous usage, the pH 7.5 run retained 28% of its maximum isomerase bed activity with a productivity of 3,011. The pH 8.5 run had deteriorated to a 21% activity rating after 833 hours with a productivity of only 838.

EXAMPLE III

The Example II pH 7.5 run was repeated at different isomerization temperatures ranging between 55° to 65° C. The initial isomerase activity at 65° C. was appreciably higher than at 60° C. (1.5 times greater), but upon prolonged usage its productivity and activity was substantially below the Example II pH 7.5 run. Calculated productivities at different operational temperatures and continuously conducted until the isomerase bed activity had decreased to 10% of their respective initial activity ratings were 6,994 at 55° C., 6.295 at 56° C., 5,670 at 57° C., 5,110 at 58° C., 4,608 at 59° C., 4,158 at 60° C., 3,754 at 61° C., 3,392 at 62° C., 3,066 at 63° C., 2,773 at 64° C., and 2,510 at 65° C. Column operation at temperatures from 55° C. to 60° C. result in a total fructose production yield increase ranging from 179% to 66% over those obtained at 65° C.

Since many embodiments of this invention may be made and since many changes may be made in the embodiments described, the foregoing is interpreted as illustrative and the invention is defined by the claims appended hereafter.

What is claimed is:

1. A process for increasing fructose yields in a continuous glucose isomerization process employing a fixed bed of immobilized glucose isomerase in which the immobilized isomerase is characterized as being obtained from the Bacillus genera and exhibiting an enhanced rate of isomerizing dextrose to fructose when the glucose isomerization reaction is conducted: (a) in the presence of Co++ ions and (b) at a temperature greater than about 60° C., said process comprising:
  (A) providing a refined monosaccharide feed syrup which is essentially free from Co++ ions and containing on a total dry solids weight basis at least 90% monosaccharide;
  (B) isomerizing the feed syrup to fructose by continuously passing the syrup through a bed of immobilized glucose isomerase at an isomerization temperature ranging from about 55° C. to 61° C. and an isomerization pH from 7.0–7.5;
  (C) recovering the isomerized syrup while replenishing the bed with a compensatory amount of feed syrup; and
  (D) continuing the feed syrup isomerization in said bed with said isomerase for at least 2,000 hours, while maintaining the isomerization temperature from about 55° C. to 61° C. and the pH from 7.0 to 7.5 for at least 90% of the operational time said bed is used to isomerize said feed syrup; and
  (E) terminating the isomerization after the isomerase activity of said bed is less than 20% of its optimum activity level.

2. The process according to claim 1 wherein the monosaccharide isomerization in said bed with said isomerase is continued for more than 3,000 hours.

3. The process according to claim 2 wherein for more than 95% of the operational time the isomerization is conducted at a pH from 7.0 to 7.5, and a temperature from 58° C. to 61° C.

4. The process according to claim 1 wherein the feed syrup has a dextrose content of at least 95% (dry substance basis) and a dry solids content ranging from about 50 to about 55% by weight.

5. The process according to claim 4 wherein the dextrose feed syrup isomerization is conducted in the presence of an isomerase derived from *Bacillus coagulans*.

6. The process according to claim 1 wherein the monosaccharide content of the feed syrup is at least 95% (dry substance weight basis) and the feed syrup is isomerized in said bed with said isomerase for more than 3,500 hours.

7. The process according to claim 6 wherein the feed syrup contains at last 0.002 M magnesium ion.

8. The process according to claim 1 wherein with no more than 5% of the total operational time is the pH above a pH 8.0 or below a pH 6.5.

9. The process according to claim 8 wherein the feed syrup is characterized as having a monosaccharide content on a dry substance weight basis of at least 92%, a magnesium ion content from about 0.003 M to about 0.01 M, and a dry solids weight content from about 45% to about 55%.

10. The process according to claim 9 wherein the feed syrup isomerization with said isomerase is continued for at least 3,000 hours.

11. The process according to claim 10 wherein the isomerase is derived from *Bacillus coagulans* and the feed syrup isomerization is continued until the isomerase bed activity reduces to less than 15% of the optimum isomerase activity of said bed.

* * * * *

UNITED STATES PATENT AND TRADEMARK OFFICE
CERTIFICATE OF CORRECTION

PATENT NO. : 4,310,628
DATED : January 12, 1982
INVENTOR(S) : Roger S. Leiser

It is certified that error appears in the above-identified patent and that said Letters Patent are hereby corrected as shown below:

Column 7, line 3 for "A typically" read ---Atypically---
Table I, in column headed "EFF. pH" the 9th figure, for "7.2" read ---7.3---
Column 13, line 38, for "cabaltous" read ---cobaltous---
Column 14, Example III, line 24, for "6.295" read ---6,295---

Signed and Sealed this

Fourth Day of May 1982

[SEAL]

Attest:

Attesting Officer

GERALD J. MOSSINGHOFF

Commissioner of Patents and Trademarks